United States Patent
Bitar

(10) Patent No.: US 11,311,367 B2
(45) Date of Patent: *Apr. 26, 2022

(54) TISSUE-ENGINEERED GUT-SPHINCTER COMPLEXES AND METHODS OF MAKING THE SAME

(71) Applicant: Wake Forest University Health Sciences, Winston-Salem, NC (US)

(72) Inventor: Khalil Bitar, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/066,233

(22) Filed: Oct. 8, 2020

(65) Prior Publication Data

US 2021/0137668 A1  May 13, 2021

Related U.S. Application Data

(60) Continuation of application No. 16/066,492, filed on Jun. 27, 2018, now abandoned, which is a
(Continued)

(51) Int. Cl.
*A61F 2/04* (2013.01)
*A61F 2/00* (2006.01)
(Continued)

(52) U.S. Cl.
CPC .............. *A61F 2/04* (2013.01); *A61F 2/0004* (2013.01); *A61F 2/08* (2013.01); *A61K 35/34* (2013.01);
(Continued)

(58) Field of Classification Search
CPC .. A61F 2/04; A61F 2/0004; A61F 2/08; A61F 2002/045; C12N 5/0697;
(Continued)

(56) References Cited

U.S. PATENT DOCUMENTS

| 4,505,266 A | 3/1985 | Yannas et al. |
| 5,190,878 A | 3/1993 | Wilhelm |

(Continued)

FOREIGN PATENT DOCUMENTS

| JP | 2004528101 A | 9/2004 |
| WO | 0149827 A1 | 7/2001 |

(Continued)

OTHER PUBLICATIONS

Raghavan, el (Gastroenterology. "Successful Implantation of Bioengineered, Intrinsically Innervated, Human Internal Anal Sphincter" Jul. 2011 ; 141(1): 310-319. (Year: 2011).*

(Continued)

*Primary Examiner* — Brian A Dukert
*Assistant Examiner* — Rebecca Lynee Zimmerman
(74) *Attorney, Agent, or Firm* — Nelson Mullins Riley & Scarborough LLP; Reza Mollaaghababa; Andrew W. Schultz

(57) ABSTRACT

Methods are disclosed for forming tissue engineered, tubular gut-sphincter complexes from intestinal circular smooth muscle cells, sphincteric smooth muscle cells and enteric neural progenitor cells. The intestinal smooth muscle cells and neural progenitor cells can be seeded on a mold with a surface texture that induces longitudinal alignment of the intestinal smooth muscle cells and co-cultured until an innervated aligned smooth muscle sheet is obtained. The innervated smooth muscle sheet can then be wrapped around a tubular scaffold to form an intestinal tissue construct. Additionally, the sphincteric smooth muscle cells and additional enteric neural progenitor cells can be mixed in a biocompatiable gel solution, and the gel and admixed cells applied to a mold having a central post such that the sphinteric smooth muscle and neural progenitor cells can be cultured to form an innervated sphincter construct around (Continued)

Engineered sphincter-rectal cuff pre-implantation the mold post. This innervated sphincter construct can also be transferred to the tubular scaffold such that the intestinal tissue construct and sphincter construct contact each other, and the resulting combined sphincter and intestinal tissue constructs can be further cultured about the scaffold until a unified tubular gut-sphincter complex is obtained.

6 Claims, 11 Drawing Sheets

Related U.S. Application Data continuation-in-part of application No. 15/976,569, filed as application No. PCT/US2016/068891 on Dec. 28, 2016, and a division of application No. 14/375,812, filed as application No. PCT/US2013/024080 on Jan. 31, 2013.

(60) Provisional application No. 62/273,161, filed on Dec. 30, 2015, provisional application No. 61/592,890, filed on Jan. 31, 2012, provisional application No. 61/592,871, filed on Jan. 31, 2012.

(51) Int. Cl.
  C12N 5/071    (2010.01)
  A61F 2/08     (2006.01)
  A61L 27/20    (2006.01)
  A61L 27/38    (2006.01)
  A61K 35/34    (2015.01)

(52) U.S. Cl.
  CPC ............ *A61L 27/20* (2013.01); *A61L 27/383* (2013.01); *A61L 27/3826* (2013.01); *A61L 27/3834* (2013.01); *A61L 27/3873* (2013.01); *A61L 27/3886* (2013.01); *C12N 5/0697* (2013.01); *A61F 2002/045* (2013.01); *A61L 2430/30* (2013.01); *C12N 2501/11* (2013.01); *C12N 2501/115* (2013.01); *C12N 2502/088* (2013.01); *C12N 2502/1347* (2013.01)

(58) Field of Classification Search
  CPC .......... C12N 2501/11; C12N 2501/115; C12N 2502/1347; C12N 2502/088; A61K 35/34; A61L 27/20; A61L 27/3826; A61L 27/383; A61L 27/3834; A61L 27/3873; A61L 27/3886; A61L 2430/30
  See application file for complete search history.

(56) References Cited

U.S. PATENT DOCUMENTS

| | | | |
|---|---|---|---|
| 5,231,169 | A | 7/1993 | Constantz et al. |
| 5,605,835 | A | 2/1997 | Hu et al. |
| 5,688,687 | A | 11/1997 | Palsson et al. |
| 5,888,807 | A | 3/1999 | Palsson et al. |
| 5,985,653 | A | 11/1999 | Armstrong et al. |
| 6,001,642 | A | 12/1999 | Tsao |
| 6,419,920 | B1 | 7/2002 | Mineau-Hanschke |
| 7,029,689 | B2 | 4/2006 | Berglund et al. |
| 7,368,279 | B2 | 5/2008 | Bitar et al. |
| 9,675,646 | B2 | 6/2017 | Bitar |
| 9,862,924 | B2 | 1/2018 | Bitar |
| 9,896,656 | B2 | 2/2018 | Bitar |
| 9,993,505 | B2 | 6/2018 | Bitar |
| 10,377,985 | B2 | 8/2019 | Bitar |
| 2003/0031651 | A1 | 2/2003 | Lee et al. |
| 2003/0072741 | A1 | 4/2003 | Berglund et al. |
| 2003/0113812 | A1 | 6/2003 | Hemperly |
| 2004/0197375 | A1 | 10/2004 | Rezania et al. |
| 2005/0209687 | A1 | 9/2005 | Sitzmann et al. |
| 2006/0134076 | A1 | 6/2006 | Bitar et al. |
| 2006/0153815 | A1 | 7/2006 | Seyda et al. |
| 2007/0025972 | A1 | 2/2007 | Rodriguez |
| 2007/0128171 | A1 | 6/2007 | Tranquillo et al. |
| 2007/0269481 | A1 | 11/2007 | Li et al. |
| 2007/0275362 | A1 | 11/2007 | Edinger |
| 2008/0031850 | A1 | 2/2008 | Bader |
| 2008/0102438 | A1 | 5/2008 | Yannas et al. |
| 2009/0317416 | A1 | 12/2009 | Mamula |
| 2010/0010290 | A1 | 1/2010 | Stephens et al. |
| 2010/0131075 | A1 | 5/2010 | Ludlow et al. |
| 2010/0184183 | A1 | 7/2010 | Schussler |
| 2011/0151011 | A1 | 6/2011 | Flynn |
| 2014/0271905 | A1 | 9/2014 | Bitar |
| 2014/0377232 | A1 | 12/2014 | Bitar |
| 2014/0379083 | A1 | 12/2014 | Bitar |
| 2016/0017285 | A1 | 1/2016 | Bitar |
| 2016/0134076 | A1 | 5/2016 | Arai et al. |
| 2017/0319325 | A1 | 11/2017 | La Francesca et al. |
| 2018/0093016 | A1 | 4/2018 | Bitar |
| 2018/0155684 | A1 | 6/2018 | Bitar |
| 2018/0256647 | A1 | 9/2018 | Bitar |
| 2019/0015190 | A1 | 1/2019 | Bitar |
| 2020/0024572 | A1 | 1/2020 | Bitar |

FOREIGN PATENT DOCUMENTS

| | | | |
|---|---|---|---|
| WO | 02087411 | A2 | 11/2002 |
| WO | 03029418 | A2 | 4/2003 |
| WO | 2010040129 | A2 | 4/2010 |
| WO | 2010072417 | A2 | 7/2010 |
| WO | 2011059920 | A2 | 5/2011 |
| WO | 2011102991 | A1 | 8/2011 |
| WO | 2011119804 | A2 | 9/2011 |
| WO | 2012064369 | A1 | 5/2012 |
| WO | 2013116446 | A1 | 8/2013 |
| WO | 2013116479 | A1 | 8/2013 |
| WO | 2014145653 | A2 | 9/2014 |
| WO | 2017117229 | A1 | 7/2017 |
| WO | 2018052953 | A1 | 3/2018 |
| WO | 2020102590 | A1 | 5/2020 |

OTHER PUBLICATIONS

Hecker et al (Am J Physiol Gastrointest Liver Physiol, "Development of a three-dimensional physiological model of the inernal anal sphincter bioengineered in vitro from isolated smooth muscle cells" (2005) 289: G188-G196, 2005. (Year: 2005).*
Of Deleyrolle et al Neural Cell Transplantation Isolation, Expansion, and Differentiation of Adult Mammalian Neural Stem and Progenitor Cells Using the Neurosphere Assay: pp. 91-101 (2009). (Year: 2009).*
U.S. Appl. No. 14/216,391, filed Mar. 17, 2014, Khalil Bitar.
U.S. Appl. No. 15/875,717, filed Jan. 19, 2018, Khalil Bitar.
U.S. Appl. No. 16/538,076, filed Aug. 12, 2019, Khalil Bitar.
U.S. Appl. No. 14/777,335, filed Sep. 15, 2015, Khalil Bitar.
U.S. Appl. No. 16/066,492, filed Jun. 27, 2018, Khalil Bitar.
U.S. Appl. No. 15/808,338, filed Nov. 9, 2017, Khalil Bitar.
U.S. Appl. No. 14/375,818, filed Jul. 31, 2014, Khalil Bitar.
U.S. Appl. No. 14/375,812, filed Jul. 31, 2014, Khalil Bitar.
U.S. Appl. No. 15/976,569, filed May 10, 2018, Khalil Bitar.
U.S. Appl. No. 17/294,312, filed May 14, 2021, Khalil Bitar.
Bagyanszki et al.,"Diabetes-Related Alterations in the Enteric Nervous System and its Microevirnment", World Journal of Diabetes, vol. 3, May 15, 2012, pp. 80-93.
Bitar et al., Receptors on smooth muscle cells: characterization by contraction and specific antagonists, Am. J. Physiol., 242:G400-G407 (1982).
Bitar, Aging and Neural Control of the GI Tract V. Aging and gastrointestinal smooth muscle: from signal transduction to contractile proteins, Am. J. Physiol., 284:GI-G7 (2003).
Bitar, HSP27 phosphorylation and interaction with actinmyosin in smooth muscle contraction, Am J. Physiol., 282: G894-G903 (2002).
Buijtenhuijs et al., "Tissue engineering of blood vessels : characterization of smooth-muscle cells for culturing on collagen-and-

(56) References Cited

OTHER PUBLICATIONS elast in based scaffods", Biotechnol. Appl Apr. 2004 vol. 39, pp. 141-149. See Abstract: materials and methods 144, 146.
Carson, Histotechnology: A Self-Instructional Text, Chicago: American Society for Clinical Pathology Press ( 1997), table of contents, 8 pages.
Dahm et al., Substance P Responsiveness of Smooth Muscle Cells is Regulated bt the Integrin Ligand Thrombospondin', Proc. Natl. Acad. Sci. USA vol. 93 Feb. 6, 1996, pp. 1276-1281.
Davis et al., Basic Methods in Molecular Biology, Elsevier (1986),table of contents, 5 pages.
Edelman, Vascular Tissue Engineering Designer Arteries, Circ. Res., 85:1115-1117 (1999).
European Extended Supplementary Search Report received in EP Application No. 14763675.7 dated Aug. 12, 2016; 9 pages.
European Office Action received in EP Application No. 13743292.8 dated Jul. 18, 2017; 6 pages.
European Search Report received in EP Application No. 13743292.8 dated Aug. 18, 2015; 7 pages.
Evers et al., Is there a nitrergic modulation of the rat external anal aSphincter? Exp Physiol vol. 98.2 (2013) pp. 397-404.
Fujimiya et al., "Peptidergic Regulation of Gastrointestinal Motility in Rodents," Peptides, vol. 21, Oct. 2000, pp. 1565-1582.
Geisbauer et al., "Transplantation of Enteric Cells into the Rodent Stomach with Basic Fibroblast Growth Factor", Cell Sci Ther; Therapy, vol. 2. Issue 1, Mar. 10, 2011, pp. 1-6.
Gilmont, RR. et al. Bioengineering of Physiologically Functional Intrinsically Innervated Human Internal Anal Sphincter Constructs. Tissue Eng. Part A. Jun. 1, 2014, vol. 20, No. 11-12, pp. 1603-1611.
Goeddel, Gene Expression Technology: Methods in Enzymology 185, Academic Press, San Diego, CA (1990), table of contents, 11 pages.
Gorenne et al., Inhibition of p42 and p44 MAP kinase does not alter smooth muscle contraction in swine carotid artery, Am. J. Physiol., 5:H131-H138 (1998).
Hansen et al., "Characterization of Collagen Thin Films for Von Willebrand Factor Binding and Platelet Ahesion," Langmuir, vol. 27, Oct. 3, 2011, pp. 13648-13658.
International Preliminary Report on Patentability and Written Opinion received in PCT/US2013/024024 dated Aug. 5, 2014; 8 pages.
International Preliminary Report on Patentability and Written Opinion, PCT/US2013/024080, dated Aug. 14, 2014 (9 pages).
International Search Report and Written Opinion received in PCT/US2014/030456 dated Aug. 29, 2014; 10 pages.
International Search Report and Written Opinion received in PCT/US2016/068891 dated Mar. 29, 2017; 9 pages.
International Search Report and Written Opinion, PCT/US2013/024024, dated May 15, 2013 (11 pages).
International Search Report and Written Opinion, PCT/US2013/024080, dated Jun. 2, 2013 (11 pages).
International Search Report and Written Opinion, PCT/US2019/061551, dated Jan. 24, 2020, 10 pages.
Japanese Office Action received in JP Application No. 2014-555699 dated Jul. 25, 2017; 5 pages.

Keef et al., Functional role of vasoactive intestinal polypeptide in inhibitory motor innervation in the mouse internal anal sphincter. J Physiol Mar. 15, 2013; 591(6): 1489-506.
L'Heureux et al., "A completely Biological Tissue-Engineered Human Blood Vessel", The FASEB Journal, vol. 12 Jan. 1998 pp. 47-56.
Madihally, Sundararajian et al. "Porous Chitosan Scaffolds for Tissue Engineering", Biomaterials 20 pp. 1133-1142 (1999).
Office Action received in U.S. Appl. No. 14/216,391 dated Feb. 3, 2017; 6 pages.
Office Action received in U.S. Appl. No. 14/777,335 dated Apr. 13, 2016; 18 pages.
Office Action received in U.S. Appl. No. 14/777,335 dated Oct. 31, 2016; 15 pages.
Office Action received in U.S. Appl. No. 16/066,492 dated Apr. 1, 2020, 11 pages.
Orlando et al., Regenerative medicine as applied to solid organ transplantation current status and future challenges. Transplant International vol. 24 No. 3 Mar. 2011 pp. 223-232.
Phillips, M. et al. Small intestine tissue sample. MedlinePlus [database online], Apr. 11, 2018. [retrieved on Jan. 6, 2020], Retrived from https://medlineplus.gov/ency/imagepages/9927.htm., p. 2.
Raghavan et al., "Bioengineered Three-Dimensional Physiological Model of Colonic Longitudinal Smooth Muscle in vitro," Tissue Engineering: Part C vol. 16 No. 5, Oct. 2010, pp. 999-1009.
Raghavan et al., Successful implantation of bioengineered, intrinsically innervated human internal anal sphincter Gastroenterology, 141, Jul. 2011 pp. 310-319.
Raghavan et al., "The Influence of Extracellular Matrix Composition on the Differentiation of Neuronal Subtypes InTissue Engineered Innervated Intestinal Smooth Muscle Sheets," Biomaterials, vol. 35, Jun. 11, 2014 pp. 7429-7440.
Raghavan et al., Neuroglial differentiation of adult enteric neuronal progenitor cells as function of extracellular matrix compositon Biomaterials, vol. 34 No. 28 Sep. 2013 pp. 6649-6658.
Somara et al., Bioengineered Internal Anal Sphincter Derived From Isolated Human Internal Anal Sphineter Muscle Cells. Gastroenterology 2009.
Tulla et al., "Selective Binding of Collagen Subtypes by Integrin Alpha 1-1, Alpha 2-1, and Alpha 10-1 Domains," The Journal of Biological Chemistry, vol. 276 No. 51 Sep. 25, 2001 pp. 48206-48212.
Ward et al., "Interstitial Cells of Cajal Mediate Cholinergic Neurotransmission From Enteric Motor Neurons," The Journal of Nueroscience vol. 20 Feb. 15, 2000 pp. 1393-1403.
Zakhem et al., "Transplantation of a human Tissue—Engineered Bowel in an Athymic Rat Model", Tissue Engineering Jun. 2017, vol. 00, pp. 1-9.
Zakhem, E et al. Successful Implantation of an Engineered Tubular Neuro-Muscular Tissue Composed of Human Cells and Chitosan Scaffold. Jun. 19, 2015; Surgery 158(6); 1598-1608.
Zhang, et al. "A Sandwich Tubular Scaffold Derived From Chitosan for Blood Vessel Tissue Engineering" Wiley Periodicals, Inc. pp. 277-284 (2006).
International Preliminary Report on Patentability, PCT/US2019/061551, dated May 27, 2021, 9 Pages.

* cited by examiner

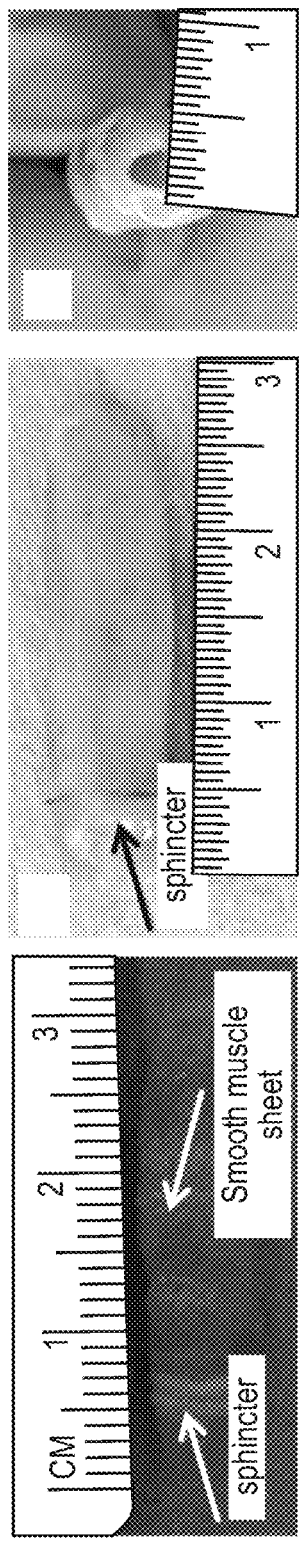

Sphincter-rectal cuff pre-implantation

Implantation subcutaneously in the abdominal area

Implantation subcutaneously in the abdominal area

Harvest after 14 days

TISSUE-ENGINEERED GUT-SPHINCTER COMPLEXES AND METHODS OF MAKING THE SAME

RELATED APPLICATIONS

This application is a continuation of U.S. application Ser. No. 16/066,492, filed Jun. 27, 2018, which is a 35 U.S.C. 371 national stage filing of International Application No. PCT/US2016/068891, filed Dec. 28, 2016, which claims priority to U.S. Provisional Application No. 62/273,161, filed Dec. 30, 2015. The present application is also a continuation-in-part of U.S. application Ser. No. 15/976,569, filed May 10, 2018, which is a divisional application of U.S. application Ser. No. 14/375,812, filed Jul. 31, 2014, now U.S. Pat. No. 9,993,505 issued Jun. 12, 2018, which is a 35 U.S.C. 371 national stage filing of International Application No. PCT/2013/024080, filed Jan. 31, 2013, which claims priority to U.S. Provisional Application No. 61/592,890, filed Jan. 31, 2012 and U.S. Provisional Application No. 61/592,871, filed Jan. 31, 2012. The contents of the aforementioned applications are hereby incorporated by reference.

GOVERNMENT RIGHTS

This invention was made with government support from National Institutes of Diabetes, Digestive and Kidney Diseases under NIH/NIDDK Grant No. RO1DK071614. The United States Government has certain rights in the invention.

FIELD OF THE INVENTION

The present invention concerns bioengineering of tubular tissue structures, such as gastrointestinal tissues and, in particular, tissue-engineered gut-sphincter complexes.

BACKGROUND

The gastrointestinal (GI) tract or "gut" is a structurally complex hollow organ that displays diverse motility patterns to perform a variety of functions that aid in ingestion, digestion, absorption of nutritive elements, and excretion of waste. Gastrointestinal motility is a result of chemical and electrical interactions between smooth muscle, intramural innervation, interstitial cells, and mucosal epithelial layers.

Phasic neuromuscular structures of the GI tract contain orthogonal layers of smooth muscle, interlaced with enteric neuronal plexuses. They are also associated with interstitial cells and specialized mucosal layers. The propagating peristaltic wave defines the phasic nature of this neuromusculature. It encompasses contraction and relaxation of both the circular and longitudinal smooth muscle layers. The neuronal components as well as the interstitial cells generate electrical activity for the coordination of peristalsis. This activity is coupled in a highly coordinated manner to intracellular biochemical events in the smooth muscle layers to result in gut motility.

The principal components of the GI tract are the small intestine, the colon and the anal sphincter. The small intestine is the primary nutrient absorptive structure of the GI tract. Peristalsis and segmental contractions of the small intestine increase the surface area to facilitate greater absorption by the villi of the intestinal epithelium. The colon is contiguous with the small intestine, facilitating water absorption, and excretion of stool. The internal anal sphincter (IAS) contributes to 70% of the anal canal closure pressure, maintaining continence. Weakened mechanical efficiency of the IAS due to idiopathic sphincteric degeneration, surgical, or obstetric trauma all lead to passive and active incontinence.

In addition to the anal sphincter, the gastrointestinal system has several other sphincters that control the transit of fluids through the gut, including the lower esophageal sphincter (LES) and the pyloric sphincter at the exit of the stomach.

In the basal state, the smooth muscle of the sphincters remains in a state of tonic contraction and closure to serve as a one-way valve to regulate flow through the opening controlled by the sphincter. Skeletal muscle sphincters are under voluntary control while smooth muscle sphincters are controlled by complex interactions between extrinsic nerves from the central nervous system (CNS) and intrinsic control by the enteric nervous system and the myogenic properties of specialized smooth muscle cells.

Sphincteric smooth muscles represent tonic muscles that remain contracted at rest and have small amplitude, slow contraction and slow relaxation response, while non-sphincteric smooth muscle represent phasic muscle that shows a wide range of contractile activity varying from a fully relaxed basal state to a large-amplitude rapid contraction and rapid relaxation response (Goyal et al., The Gastrointestinal System, Motility and Circulation, in Handbook of Physiology, J. D. Wood and S. G. Schultz, Editors. 1989, The American Physiological Society: Bethesda. p. 865-908).

There exists a need for functional tissue-engineered sphincteric constructs for repair and/or reconstruction of damaged sphincters as well as tissue engineered gut-sphincter complexes for gut-lengthening and other therapeutic interventions. Alternatively, such constructs could provide functional in vitro models of sphincters and gut segments for development of therapies and/or drug testing.

SUMMARY

Methods and constructs are disclosed for bioengineering of gastrointestinal tissue. In particular, three-dimensional, bioengineered, tubular gut-sphincter complexes are disclosed, together with methods of forming such constructs.

In one aspect, methods of forming tissue engineered, tubular gut-sphincter complexes are disclosed that start by obtaining intestinal circular smooth muscle cells from an intestinal donor source, obtaining sphincteric smooth muscle cells from a sphincteric donor source, and obtaining enteric neural progenitor cells from at least one neural progenitor donor source. The intestinal smooth muscle cells can be seeded on a mold with a surface texture that induces longitudinal alignment of the intestinal smooth muscle cells with the neural progenitor cells added to the intestinal smooth muscle cells on the mold, such that the combination of intestinal smooth muscle cells and the neural progenitor cells can be cultured until an innervated aligned smooth muscle sheet is obtained. The innervated smooth muscle sheet can then be wrapped around a tubular scaffold to form an intestinal tissue construct. Additionally, the sphincteric smooth muscle cells and additional enteric neural progenitor cells can be mixed in a biocompatiable gel solution, and the gel and admixed cells can be applied to a mold having a central post; the sphinteric smooth muscle and neural progenitor cells can be cultured to form an innervated sphincter construct around the mold post. Once formed, the innervated sphincter construct can also be transferred to the tubular scaffold such that the intestinal tissue construct and sphincter construct contact each other, and the resulting combined sphincter and intestinal tissue constructs can be further cultured about the scaffold until a unified tubular gut-sphincter complex is obtained.

In other aspects, tissue engineered, tubular gut-sphincter complexes are disclosed for therapeutic inventions or for use as screening or testing platforms, e.g., for organ on a chip purposes, to test the effects of drugs or other therapies on functional gut tissue.

BRIEF DESCRIPTION OF THE DRAWINGS

FIGS. 1A-1C are photographs of an engineered sphincter-rectal cuff complex construction. FIG. 1A is a photograph of the complex pre-implantation. FIG. 1B is a photograph of the complex construction post-implantation. FIG. 1C is a photograph of an end view of the construction, showing maintenance of luminal patency.

FIG. 3A is a photograph of an engineered sphincter-rectal cuff complex construction preimplantation. FIG. 3B is a photograph of an engineered sphincter-rectal cuff complex construction during implantation. FIG. 3C is a photograph of an engineered sphincter-rectal cuff complex construction immediately following implantation. FIG. 3D is a photograph of an engineered sphincter-rectal cuff complex construction at harvest after 14 days in the animal's abdominal cavity.

FIG. 5A is a photograph that shows the complex pre-implantation, having a gut part 3 cm in length and a sphincter part (identified by a white arrow). FIG. 5B is a photograph that shows the complex after 4 weeks of subcutaneous implantation in the abdominal wall and shows vascularization of the complex. FIG. 5C is a photograph that shows that the complex maintained its luminal patency (0.3 cm internal diameter).

FIG. 7A is a graph that shows that the tensile strength of the complex was 0.043±0.007 MPa compared to 0.067±0.006 MPa for the native rat intestine. FIG. 7B is a graph that shows that the elongation at break of the implant was 171±30% compared to 230±13% for the native rat intestine. FIG. 7C is a graph that shows that Young's modulus of the implanted complex was 0.1±0.01 MPa compared to 0.12±0.01 MPa for the native rat intestine.

FIG. 8A is an image of H&E for the sphincter. FIG. 8B is an image of H&E for the gut parts of the complex, showing maintenance of the circular alignment of the smooth muscle around the lumen of the tubular graft.

FIG. 9A shows the smooth muscle of the sphincter. FIG. 9B shows the smooth muscle of the gut parts. Together, FIG. 9A and FIG. 9B show that the sphincter and gut parts of the complex maintained their contractile phenotype as shown by positive stain for smoothelin after 4 weeks of implantation. FIG. 9C demonstrates the innervation of the complex as demonstrated by positive stain with βIII tubulin, indicating that the neural progenitor cells differentiated into neurons. FIG. 9D shows the presence of excitatory motor neurons, demonstrated by positive stain with ChAT. FIG. 9E shows inhibitory motor neurons stained positive with nNOS. FIG. 9F demonstrates vascularization by positive stain with von Willebrand factor.

FIG. 10A shows that the implanted sphincter maintained its capacity to generate a spontaneous basal tone of 382±79 μN. FIG. 10B shows that the addition of potassium chloride (KCl) resulted in a contraction of 427±42 μN above the basal tone in the sphincter. FIG. 10C shows that KCl resulted in a robust and sustained contraction (434±17 μN) in the gut part of the complex.

FIG. 11A is a graph that shows electrical field stimulation (EFS) of the sphincter. FIG. 11B is a graph that also shows electrical field stimulation (EFS) of the sphincter. FIG. 11C is a graph that shows electrical field stimulation of the gut parts of the complex. Together FIGS. 11A-11C show that electrical field stimulation caused relaxation of the smooth muscle (black trace). FIG. 11D is a graph that shows that pre-incubation of the implants with nNOS inhibitor LNAME significantly reduced the magnitude of relaxation, indicating the presence of functional nitrergic neurons (See also the grey traces of FIGS. 11B & 11C).

DETAILED DESCRIPTION

Figure 2A:
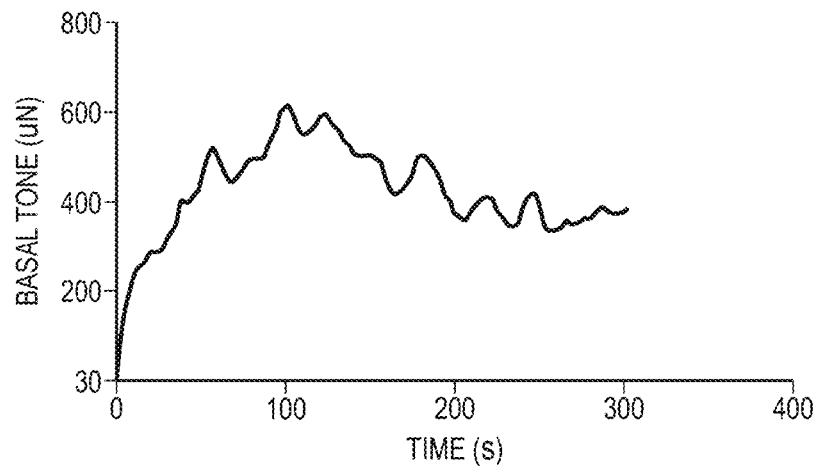
FIG. 2A is a graph of changes in basal tone over time of a an engineered sphincter-rectal cuff complex construction according to the invention during an induced contraction.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth. The steps of any method can be practiced in feasible order and are restricted to a sequential order merely because they are so recited in a claim.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

"Differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts. Neural stem cells can be isolated from embryonic and adult central nervous system (CNS) tissue, neural tube tissue or enteric nervous system (ENS) tissue.

Stem cells can be further classified according to their developmental potential as: (1) totipotent; (2) pluripotent; (3) multipotent; (4) oligopotent; and (5) unipotent. Totipotent cells are able to give rise to all embryonic and extra-embryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent typically are only able to give rise to a single cell lineage.

In a broader sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase "differentiates into a neural lineage or phenotype" refers to a cell that becomes partially or fully committed to a specific neural phenotype of the CNS or PNS, i.e., a neuron or a glial cell, the latter category including without limitation astrocytes, oligodendrocytes, Schwann cells and microglia. The term "neural" as used herein is intended to encompass all electrical active cells, e.g., cells that can process or transmit information through electrical or chemical signals, including the aforementioned neurons, glial cells, astrocytes, oligodendrocytes, Schwann cells and microglia.

For the purposes of this disclosure, the terms "neural progenitor cell" or "neural precursor cell" mean a cell that can generate progeny that are either neuronal cells (such as neuronal precursors or mature neurons) or glial cells (such as glial precursors, mature astrocytes, or mature oligodendrocytes). Typically, the cells express some of the phenotypic markers that are characteristic of the neural lineage. Typically, they do not produce progeny of other embryonic germ layers when cultured by themselves in vitro, unless dedifferentiated or reprogrammed in some fashion.

A "neuronal progenitor cell" or "neuronal precursor cell" is a cell that can generate progeny that are mature neurons. These cells may or may not also have the capability to generate glial cells. A "glial progenitor cell" or "glial precursor cell" is a cell that can generate progeny that are mature astrocytes or mature oligodendrocytes. These cells may or may not also have the capability to generate neuronal cells.

The phrase "biocompatible substance" and the terms "biomaterial" and "substrate" are used interchangeably and refer to a material that is suitable for implantation or injection into a subject. A biocompatible substance does not cause toxic or injurious effects once implanted in the subject. In one embodiment, the biocompatible substrate includes at least one component of extracellular matrix. In other embodiments, the substrate can also include a polymer with a surface that can be shaped into the desired structure that requires repairing or replacing. The polymer can also be shaped into a part of a body structure that requires repairing or replacing. In another embodiment, the biocompatible substrate can be injected into a subject at a target site.

In one embodiment, the substrate is an injectable or implantable biomaterial that can be composed of crosslinked polymer networks which are typically insoluble or poorly soluble in water, but can swell to an equilibrium size in the presence of excess water. For example, a hydrogel can be injected into desired locations within the organ. In one embodiment, the collagen can be injected alone. In another embodiment, the collagen can be injected with other hydrogels. The hydrogel compositions can include, without limitation, for example, poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), polysaccharides and mixtures thereof. Furthermore, the compositions can also include, for example, a poly(hydroxy) acid including poly(alpha-hydroxy) acids and poly(beta-hydroxy) acids. Such poly(hydroxy) acids include, for example, polylactic acid, polyglycolic acid, polycaproic acid, polybutyric acid, polyvaleric acid, and copolymers and mixtures thereof.

Hydrogels with effective pore sizes in the 10-100 nm range and in the 100 nm-10 micrometer range are termed "microporous" and "macroporous" hydrogels, respectively. Microporous and macroporous hydrogels are often called polymer "sponges." When a monomer, e.g., hydroxyethyl methacrylate (HEMA), is polymerized at an initial monomer concentration of 45 (w/w) % or higher in water, a hydrogel is produced with a porosity higher than the homogeneous hydrogels. Hydrogels can also expand in the presence of diluent (usually water). The matrix materials of present invention encompass both conventional foam or sponge materials and the so-called "hydrogel sponges." For a further description of hydrogels, see U.S. Pat. No. 5,451,613 (issued to Smith et al.) herein incorporated by reference.

The term "extracellular matrix" or "ECM" is used herein to denote compositions comprising one or more of the following: collagen I, collagen IV, laminin, heparan sulfate, or fragments of one or more of such proteins.

"Collagen I" refers to collagen I or collagen I compositions derived from cell culture, animal tissue, or recombinant means, and may be derived from human, murine, porcine, or bovine sources. "Collagen I" also refers to substances or polypeptide(s) at least substantially homologous to collagen I or collagen I compositions. Additionally, "collagen I" refers to collagen I or collagen I compositions that do not include a collagen I fragment, e.g., including essentially only a complete collagen I protein.

"Collagen IV" refers to collagen IV or collagen IV compositions derived from cell culture, animal tissue, or recombinant means, and may be derived from human, murine, porcine, or bovine sources. "Collagen IV" also refers to substances or polypeptide(s) at least substantially homologous to collagen IV or collagen IV compositions. Additionally, "collagen IV" refers to collagen IV or collagen IV compositions that do not include a collagen IV fragment, e.g., including essentially only a complete collagen I protein.

"Laminin" refers to laminin, laminin fragments, laminin derivatives, laminin analogs, or laminin compositions derived from cell culture, recombinant means, or animal tissue. "Laminin" can be derived from human, murine, porcine, or bovine sources. "Laminin" refers to laminin or laminin compositions comprising laminin-1, laminin-2, laminin-4, or combinations thereof. "Laminin" also refers to substances or polypeptide(s) at least substantially homologous to laminin-1, laminin-2, or laminin-4. Additionally, "laminin" refers to laminin or laminin compositions that do not include a laminin fragment, e.g., including essentially only a complete laminin protein.

The term "subject" as used herein refers to any living organism, including, but not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

The terms "treating," "treatment" or "intervention" refer to the administration of one or more therapeutic agents or procedures to a subject who has a condition or disorder or a predisposition toward a condition or disorder, with the purpose to prevent, alleviate, relieve, alter, remedy, ameliorate, improve, affect, slow or stop the progression, slow or stop the worsening of the disease, at least one symptom of condition or disorder, or the predisposition toward the condition or disorder.

The gut is responsible for ingestion of food, propulsion of luminal content and excretion of waste. These functions are conducted by the basic unit of the musculature of the gut, which is the smooth muscle. Function of the smooth muscle of the gut is highly regulated, mainly by the enteric nervous system (ENS) and the interstitial cells of Cajal (ICCs). The smooth muscle receives regulatory inputs which are critical to produce a coordinated response. While the gut is considered a continuous tubular muscular organ (except for the stomach), several sphincters exist as checkpoints along the length of the gut. Those sphincters possess high pressure zone that regulate the propulsion of luminal content. Neuro-muscular diseases of the gut alter the normal motility patterns. Even though surgical intervention remains the standard treatment, preservation of the sphincter attached to the rest of the gut is challenging.

Motility disorders result when neuro-muscular functions of the gut are disturbed. In certain cases of neuro-muscular diseases, sphincter integrity and function is also impaired. In esophageal achalasia, impairment of the enteric neurons at the level of the smooth muscle of the lower esophagus causes loss of relaxation of the lower esophageal sphincter (LES). Treatments aim to reduce the contractility of the LES. This can be done using different drugs/blockers, balloon dilatation, injection of botulinum toxin or myotomy of the LES. On the other hand, gastroparesis is characterized by delayed gastric emptying. This is partially attributed to the inability of the pyloric sphincter to relax. Common treatments include botulinum toxin injection, drugs/diet change, gastric electric stimulation or pyloroplasty. In patients with colorectal cancer, preservation of the sphincter following surgical resection of the tumor is challenging. The formation of a stoma is a common treatment; however patients suffer from low quality of life (social and physical problems). In other cases, congenital anomalies such as anorectal malformation involve the rectum along with the anus. Children with anorectal malformation require surgical intervention which consists of either surgical repair or a colostomy. Fecal incontinence is a major complication among other physical and social morbidities resulting from anorectal malformation. All of the listed treatments for neuro-muscular disorders are either associated with complications or provide a short-term relief for the patients. New long term therapeutic strategies are needed.

Methods and constructs are disclosed for bioengineering of gastrointestinal tissue. In particular, three-dimensional, bioengineered, tubular gut-sphincter complexes (TGSC) are disclosed, together with methods of forming such constructs. Specifically, engineered innervated human smooth muscle sheets and innervated human sphincters with a pre-defined alignment are disclosed for placement around tubular scaffolds to create a gut-sphincter complex.

In certain embodiments, a method of forming a tissue engineered, tubular gut-sphincter complex comprises: isolating intestinal circular smooth muscle cells from an intestinal donor source, isolating sphincteric smooth muscle cells from a sphincteric donor source, isolating enteric neural progenitor cells from at least one neural progenitor donor source, seeding the isolated intestinal circular smooth muscle cells on a mold with a surface texture that induces longitudinal alignment of the intestinal circular smooth muscle cells, adding the isolated enteric neural progenitor cells to the intestinal circular smooth muscle cells on the mold, co-culturing the intestinal circular smooth muscle cells and the enteric neural progenitor cells until an innervated aligned smooth muscle sheet is obtained, disposing the innervated aligned smooth muscle sheet around a tubular scaffold to form an innervated intestinal tissue construct, admixing the sphincteric smooth muscle cells and additional enteric neural progenitor cells in a biocompatible gel solution, applying the gel and admixed cells to a mold having a central post; co-culturing the sphincteric smooth muscle cells and neural progenitor cells to form an innervated sphincter construct around the mold post, transferring and applying the innervated sphincter construct to the tubular scaffold such that the innervated intestinal tissue construct and the innervated sphincter construct contact each other, and further culturing the combined sphincter and intestinal tissue constructs about the scaffold until a unified tubular gut-sphincter complex is obtained.

In embodiments described herein, the steps of isolating the intestinal circular smooth muscle cells, sphincteric smooth muscle cells and enteric neural progenitor cells may further comprise obtaining each type of cell from a single subject. In some embodiments, the intestinal circular smooth muscle cells, sphincteric smooth muscle cells and enteric neural progenitor cells are obtained from a subject who is between the ages of about 1 year to about 80 years.

In embodiments described herein, at least one co-culturing step may comprise culturing cells in a collagen suspension.

In embodiments described herein, the step of disposing the innervated aligned smooth muscle sheet around a tubular scaffold may comprise wrapping the innervated aligned smooth muscle sheet around a chitosan scaffold.

In embodiments described herein, the method of forming a tissue engineered, tubular gut-sphincter complex may further comprise connecting two or more innervated aligned smooth muscle sheets together to form a composite structure.

In some embodiments, the unified tubular gut-sphincter complex has a length of about 1 cm to about 100 cm. In certain embodiments, the unified tubular gut-sphincter complex has a width of about 0.1 cm to about 10 cm.

In certain embodiments, a tubular gut-sphincter complex is formed by isolating intestinal circular smooth muscle cells from an intestinal donor source, isolating sphincteric smooth muscle cells from a sphincteric donor source, isolating enteric neural progenitor cells from at least one neural progenitor donor source, seeding the isolated intestinal circular smooth muscle cells on a mold with a surface texture that induces longitudinal alignment of the intestinal circular smooth muscle cells, adding the isolated enteric neural progenitor cells to the intestinal circular smooth muscle cells on the mold, co-culturing the intestinal circular smooth muscle cells and the enteric neural progenitor cells until an innervated aligned smooth muscle sheet is obtained, disposing the innervated aligned smooth muscle sheet around a tubular scaffold to form an innervated intestinal tissue construct, admixing the sphincteric smooth muscle cells and additional enteric neural progenitor cells in a biocompatiable gel solution, applying the gel and admixed cells to a mold having a central post; co-culturing the sphinteric smooth muscle cells and neural progenitor cells to form an innervated sphincter construct around the mold post, transferring and applying the innervated sphincter construct to the tubular scaffold such that the innervated intestinal tissue construct and the innervated sphincter construct contact each other, and further culturing the combined sphincter and intestinal tissue constructs about the scaffold until a unified tubular gut-sphincter complex is obtained.

In embodiments described herein, steps of isolating the intestinal circular smooth muscle cells, sphincteric smooth muscle cells and enteric neural progenitor cells in the formation of the tubular gut-sphincter complex may further comprise obtaining each type of cell from a single subject. In some embodiments, the intestinal circular smooth muscle cells, sphincteric smooth muscle cells and enteric neural progenitor cells are obtained from a subject who is between the ages of about 1 year to about 80 years.

In embodiments described herein, in the formation of the tubular gut-sphincter complex at least one co-culturing step may comprise culturing cells in a collagen suspension.

In embodiments described herein, in the formation of the tubular gut-sphincter complex the step of disposing the innervated aligned smooth muscle sheet around a tubular scaffold may comprise wrapping the innervated aligned smooth muscle sheet around a chitosan scaffold.

In embodiments described herein, the formation of a tissue engineered, tubular gut-sphincter complex may further comprise connecting two or more innervated aligned smooth muscle sheets together to form a composite structure.

In some embodiments, the tubular gut-sphincter complex has a length of about 1 cm to about 100 cm. In certain embodiments, the unified tubular gut-sphincter complex has a width of about 0.1 cm to about 10 cm.

In certain embodiments, a tubular gut-sphincter complex comprises: a tubular scaffold; an innervated intestinal tissue construct disposed about the tubular scaffold; and an innervated sphincteric tissue construct also disposed about the tubular scaffold joined to the intestinal tissue construct at an end of the intestinal tissue construct; and the complex exhibits directionally oriented smooth muscle cells, basal tone and choleric contractions in response to a contractile stimulus.

In embodiments described herein, the tubular scaffold may further comprise a chitosan scaffold.

In some embodiments, the tubular gut-sphincter complex has a length of about 1 cm to about 100 cm. In certain embodiments, the unified tubular gut-sphincter complex has a width of about 0.1 cm to about 10 cm.

To demonstrate the utility of the present invention, engineered complexes were subcutaneously implanted in the abdomen of the rats for 4 weeks. The implanted tissues exhibited vascularization and in vivo manometry revealed luminal pressure at the gut and the sphincter zone. Tensile strength, elongation at break and Young's modulus of the engineered complexes were similar to those of native rat intestine. Histological and immunofluorescence assays showed maintenance of smooth muscle circular alignment in the engineered tissue, maintenance of smooth muscle contractile phenotype and innervation of the smooth muscle. Electrical field stimulation induced a relaxation of the smooth muscle of both the sphincter and the gut parts. Relaxation was partially inhibited by nitric oxide inhibitor indicating nitrergic contribution to the relaxation. The sphincteric part of TGSC maintained the basal tone characteristic of a native sphincter. The gut part also maintained its specific neuro-muscular characteristics. The results of this study provide a promising therapeutic approach to restore gut continuity and motility.

EXAMPLe 1

Spincter-Rectal Cuff Complex

Innervated aligned smooth muscle sheets were engineered using the co-culture technique of isolated human smooth muscle cells and human enteric neural progenitor cells derived from the small intestine, as described above. The sheets were wrapped around tubular chitosan scaffolds. Innervated pyloric sphincters were engineered using human pyloric smooth muscle and enteric neural progenitor cells, again as described above. The sphincters were placed on one end around the tubular scaffold. The combination of the tissues around the tubular scaffold is referred to as sphincter-rectal cuff. The sphincter-rectal cuff was 3 cm in length and 3 mm internal diameter.

Figure 5A:
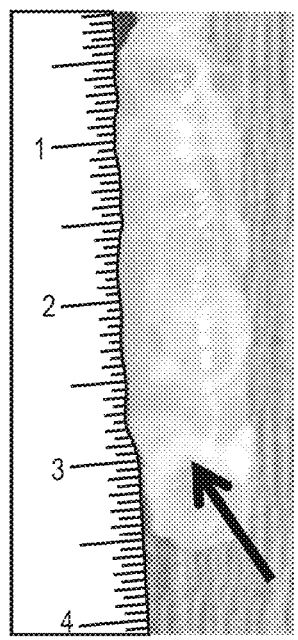
FIGS. 5A-5C are photographs of a gut-sphincter complex according to the invention.

Athymic rats were used for this study to avoid implant rejection since the implant was made of human cells. Following sedation of the rats, a 5 cm midline skin incision was made. The engineered tubular tissue was implanted subcutaneously and fixed in place using non-resorbable sutures. FIG. 5A is a photograph of bioengineered sphincter-rectal cuff pre-implantation.

Four weeks following implantation, the rats were brought to the procedure room and anesthetized using isoflurane. A midline incision was made and the surgical site was re-accessed. The implanted sphincter-rectal cuff was healthy in color and highly vascularized The implant maintained its luminal patency for 4 weeks. A manometry catheter was used to measure the luminal pressure in the sphincter-rectal cuff. The sensors were linearly aligned along the catheter and were 2 mm apart. The catheter was inserted into the lumen of the sphincter-rectal cuff while still attached under the skin. Luminal pressure was recorded in all 3 channels and averaged 40 mmHg. Spontaneous small amplitude contractions were seen in all 3 channels. The rat was then euthanized and the implant was harvested.

Figure 2B:
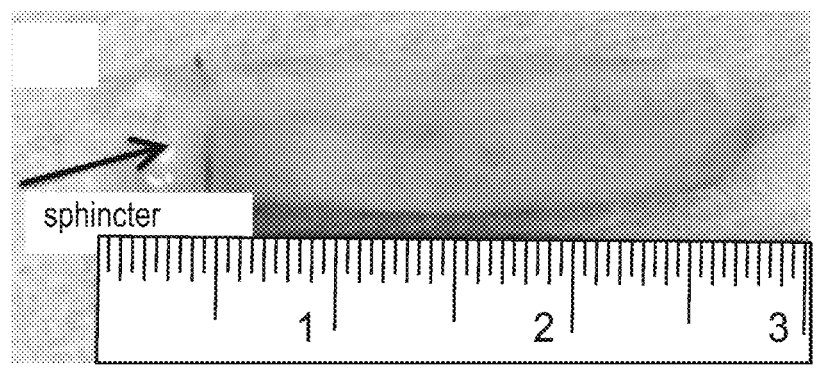
FIG. 2B is a photograph of the sphincter-rectal cuff complex with the sphincter component delineated.
Figure 3A:
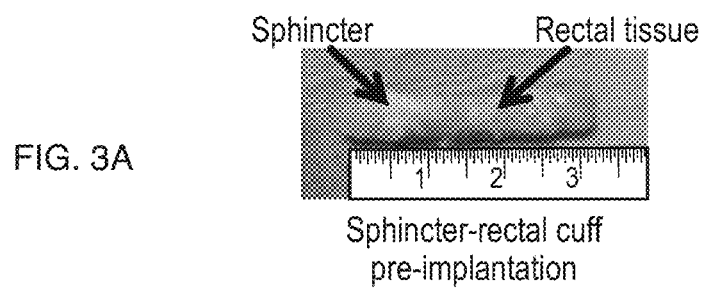
FIGS. 3A-3D are further photographs of a sphincter-rectal cuff complex.
Figure 3B:
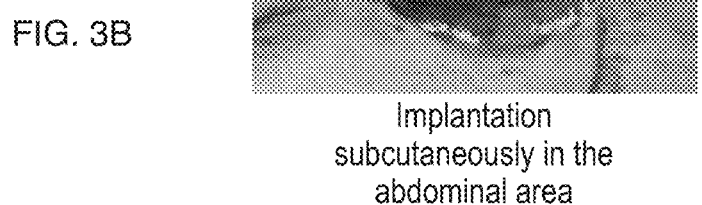
Figure 3C:
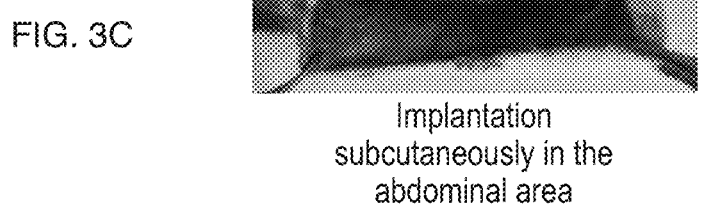
Figure 3D:
Figure 4:
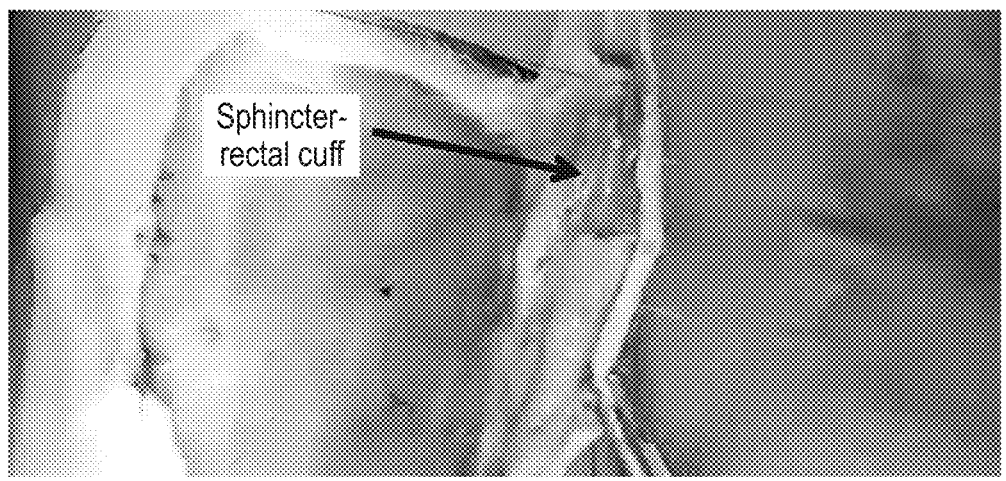
FIG. 4 is another photograph of a sphincter-rectal cuff complex following implantation.

FIGS. 1A-1C are photographs of an engineered sphincter-rectal cuff complex construction. FIG. 1A shows the complex pre-implantation while FIG. 1B shows the complex construction post-implantation and FIG. 1C is an end view the construction, showing maintenance of luminal patency. FIG. 2A is a graph of changes in basal tone over time during an induced contraction. FIG. 2B is a photograph of the sphincter-rectal cuff complex with the sphincter component delineated. FIGS. 3A-3D are further photographs of a sphincter-rectal cuff complex preimplantation (FIG. 3A), during implantation (FIG. 3B), immediately following implantation (FIG. 3C) and at harvest after 14 days in the animals abdominal cavity (FIG. 3D). FIG. 4 is another photograph of sphincter-rectal cuff complex following implantation.

Following measurement of luminal pressure, one end of the sphincter-rectal cuff was tightly clamped while the other end was left open. A volume of 1 ml of liquid was pipetted through the open end. The tissue expanded in the center as it was filled with liquid. The tissue then returned to its original shape after the liquid solution was cleared. There was no sign of leakage or disruption.

Cross sections of the sphincter and the rectal cuff were used for physiological studies. The sphincter maintained its ability to generate a spontaneous basal tone similar to an engineered sphincter prior to its implantation. This indicates that the implanted sphincter maintains its tonic characteristic in vivo. The electromechanical coupling integrity of the smooth muscle was also evaluated in the presence of potassium chloride. Following depolarization of the smooth muscle membrane in both the sphincter and the rectal cuff, a fast and robust contraction was observed. This indicates that the voltage-dependent calcium channels were maintained in the sphincter-rectal cuff after 4 weeks of implantation. Next, we evaluated the response of the sphincter-rectal cuff to exogenous neurotransmitters. The addition of acetylcholine (Ach) caused a rapid contraction, which was significantly attenuated when the tissue was pre-treated with the neurotoxin tetrodotoxin (TTX). This indicates that Ach acted on both the smooth muscle and the neurons and caused muscle contraction. After blocking the neurons with TTX, Ach acted on smooth muscle receptors only and caused a lower response. Relaxation was evaluated in the presence of VIP (vasoactive intestinal polypeptide). In the presence of TTX, the observed VIP-induced relaxation was significantly diminished. Again, this indicates that VIP relaxation was mediated through receptors on the smooth muscle and neurons. To further confirm the functionality of the neurons, electrical field stimulation (EFS) was applied on the implant. EFS caused a rapid relaxation which was completely inhibited by TTX. This indicated that the response was purely neuronally mediated.

Additional cross sections of the sphincter and the rectal cuff were fixed in formalin and processed for histological analysis. H&E staining showed maintenance of alignment of smooth muscle around the lumen of the tubular scaffold. Maintenance of smooth muscle phenotype was confirmed by positive immunostaining for smooth muscle specific markers. Innervation was also confirmed by positive satining for neural marker βIII tubulin. Vascularization was further confirmed by staining for von Willebrand factor.

Cross sections of the implanted tissue were obtained and were mechanically evaluated using a mechanical testing machine (Instron). The tissues were subjected to tensile stress and strain testing. Young's modulus of the implant was higher than the scaffold only, indicating that the innervated smooth muscle sheet remodeled around the scaffold following implantation resulting in higher Young's modulus. This is an indication that the implant was able to handle higher stretch without breaking when compared to scaffolds only.

EXAMPLE 2

Sphincter-Intestine Complex

Materials and Methods:

Cell culture reagents were purchased from Life Technologies (Grand Island, N.Y., US) unless otherwise specified. Smooth muscle growth medium consisted of Dulbecco's modified Eagle medium, 10% fetal bovine serum, 1.5% antibiotic-antimycotic, and 0.6% L-glutamine. Neural growth medium consisted of neurobasal, 1×N2 supplement, recombinant human Epidermal Growth Factor (EGF 20 ng/mL, Stemgent, San Diego, Calif., US), recombinant basic Fibroblast Growth Factor (bFGF 20 ng/mL, Stemgent, Calif., US), and 1×antibiotic-antimycotic. Neural differentiation media consisted of neurobasal medium-A supplemented with 2% fetal bovine serum, 1×B27 supplement and 1×antibiotic-antimycotic. Medium molecular weight chitosan (75-85% deacetylation), tetrodotoxin (TTX), and neuronal nitric oxide synthase (nNOS)-blocker $N_{\omega}$-Nitro-L-arginine methyl ester hydrochloride (L-NAME) were purchased from Sigma (St. Louis, Mo.). Sylgard [poly (dimethylsiloxane); PDMS] was purchased from World Precision Instruments (Sarasota, Fla.). Type I rat tail collagen was purchased from BD Biosciences.

Human intestinal and pyloric tissues were ethically obtained from organ donors through Carolina Donor Services and Wake Forest Baptist Medical Center (IRB No. 00007586). Tissues were obtained from three donors aged 2, 18, and 67 years.

Human intestinal circular smooth muscle cells: Smooth muscle cells were isolated from human duodenum. The duodena (10 cm below the pyloric sphincter) were obtained consistently for cell isolation. Human duodena were cleaned of any luminal content and were washed extensively in ice-cold Hank's balanced salt solution (HBSS). The tissues were cut into smaller pieces and the circular smooth muscle was obtained by stripping off the mucosa and the longitudinal muscle. The circular smooth muscle tissue was then minced, washed extensively in HBSS and incubated in a digestion mix containing type II collagenase (Worthington, Lakewood, N.J.) and DNAse (Roche, Indianapolis, Ind.) for one hour at 37° C. with agitation. The digested tissue was then extensively washed in HBSS and subjected to a second digest. Digested cells were washed, resuspended in warm smooth muscle growth media and expanded in tissue culture flasks at 37° C. with 5% $CO_2$.

Human pyloric smooth muscle cells: Human pylori were dissected off for smooth muscle isolation. Pylorus tissues were cleaned of any fat and mucosa and extensively washed with HBSS. Tissues were then minced and washed again with sterile HBSS. Minced tissues were digested twice at 37° C. with agitation in type II collagenase (Worthington Biochemical, Lakewood, N.J.) and DNAse (Roche, Indianapolis, Ind.) for one hour each. Cells were pelleted down with centrifugation, resuspended in smooth muscle growth media and expanded in tissue culture flasks at 37° C. with 5% $CO_2$.

Human enteric neural progenitor cells: Human enteric neural progenitor cells were isolated from the small intestine. Human duodenal tissues were finely minced followed by extensive washing in HBSS. Tissues were then digested in a mixture of type II collagenase, dispase, and DNAse. The cells were passed through 70 μm cell strainer followed by extensive washing. The cells were then passed through 40 μm cell strainers. Following centrifugation, cells were resuspended in neural growth media and cultured in non-tissue culture treated plates at 37° C. and 7% $CO_2$. The cultured cells formed free-floating clusters referred to as neurospheres which have been shown to stain positive for neural crest-derived cell marker p75.

Preparation of tubular gut-sphincter segment: Tubular chitosan/collagen scaffolds were engineered as described by Zakhem et al. in "Chitosan-based scaffolds for the support of smooth muscle constructs in intestinal tissue engineering," *Biomaterial*, 2012; 33:4810-7 and Zakhem et al. in "Development of Chitosan Scaffolds with Enhanced Mechanical Properties for Intestinal Tissue Engineering Applications," *Journal of Functional Biomaterials*, 2015; 6:999-1011. A 2% w/v chitosan solution was prepared in 0.2 M acetic acid. The chitosan solution was then mixed with type I collagen in a 1:1 ratio. The mix was then poured into a custom-made 3-cm long tubular mold with a diameter of 0.7 cm. The lumen of the scaffold was created by inserting an inner tubing of 0.3 cm diameter in the center of the main tubular mold. This created a scaffold with length of 3 cm and internal diameter of 0.3 cm. The scaffolds were frozen at −80° C. for 3 hours followed by lyophilization overnight. The scaffolds were then neutralized in 0.2 NaOH and washed extensively with PBS and distilled water. The scaffolds were sterilized in 70% ethanol and then washed extensively with sterile 1× PBS before cell seeding.

Innervated aligned smooth muscle sheets were engineered as previously described by Zakhem et al. in "Successful implantation of an engineered tubular neuromuscular tissue composed of human cells and chitosan scaffold," *Surgery*, 2015; 158:1598-608. and Zakhem et al. in "Development of Chitosan Scaffolds with Enhanced Mechanical Properties for Intestinal Tissue Engineering Applications," *Journal of Functional Biomaterials*, 2015; 6:999-1011. Briefly, smooth muscle cells were seeded onto wavy molds made of Sylgard with longitudinal grooves and allowed to align. Five days after smooth muscle alignment, neural progenitor cells were collected and suspended in a mixture of 10% FBS, 1× DMEM, 1× antibiotic-antimycotic, 10 m/ml mouse laminin and 0.4 mg/ml type I rat tail collagen. Neural progenitor cells were then mixed in collagen/laminin gel and laid on top of the smooth muscle. Engineered human innervated smooth muscle sheets were then circumferentially wrapped around the tubular scaffolds as described previously to mimic the circular muscle layer. The sheets around the scaffolds are referred to as the gut part of the complex. Human innervated pyloric smooth muscle sphincters were engineered as previously described by Rego et al. in "Bioengineered human pyloric sphincters using autologous smooth muscle and neural progenitor cells," *Tissue engineering*, 2015. A suspension of 200 000 enteric neural progenitor cells was suspended in a gel mix. The mixture was pipetted on a Sylgard-coated plate that had a central cylindrical post and allowed to gel for about 20 min at 37° C. Pyloric smooth muscle cells were trypsinized and 500 000 cells were obtained. The cells were resuspended in a similar gel mixture. The mixture was then pipetted on top of the first neural layer. Following gelation, differentiation media was supplemented every other day for 10 days. The sphincters were also placed, at one end, around the tubular scaffolds and were referred to as the sphincter part of the complex.

Implantation of the engineered tubular gut-sphincter complex: Athymic rats (n=6) were used as recipients of the tubular gut-sphincter complexes. Surgical procedures described in this work were performed following the guidelines set forth by IACUC. Rats were anesthetized by continuous isoflurane masking throughout the surgery. The surgical area was shaved and aseptically prepared. A midline skin incision of up to 5 cm was made in the abdominal wall. The engineered tubular gut-sphincter complex was fixed using 5-0 prolene sutures to mark the tissue at the time of harvest. The rats were allowed to recover in their cages in standard fashion and were given the appropriate analgesics.

In vivo intraluminal pressure measurement: Four weeks following implantation, the rats were brought back to the procedure room. The rats were anesthetized by continuous isoflurane masking. The surgical site was re-accessed. The implants were located by the prolene sutures. An air-charged catheter with circumferential sensors (7 mm spacing between the sensors) was used to measure the luminal pressure of the tubular implants. The catheter was inserted into the tubular implant entering from the gut part until the first sensor of the catheter reached the sphincteric area. The remaining sensors measured the pressure at the gut part of the tubular implant. Luminal pressure was recorded using InSIGHT Acquisition (version 5.2.4, Sandhill scientific Inc, Highland Ranch, Colo., USA). The recorded pressures were analyzed using BioVIEW system (version 5.6.3.0 Sandhill scientific Inc, Highland Ranch, Colo., USA). Following pressure readings, the rats were euthanized. The implants were dissected from the surrounding tissue. The harvested implants were further evaluated.

Immediately after harvest, the implants were tested for their tensile properties using a uniaxial load test machine (Instron model #5544, Issaquah, Wash., USA). Tubular specimens were obtained and hooked onto the machine equipped with a 2 kN load cell. Tensile strength, elongation at break and Young's modulus were obtained. Rat native intestines served as control.

A pressure transducer catheter with an inflatable balloon was used to measure the burst strength pressure of the implants. The catheter was inserted into the lumen of the implants and the luminal pressure was increased until failure occurred. The pressure was slowly increased until failure occurred and the pressures were recorded.

Immediately after harvest, sections of the sphincter and the gut tissues were fixed in formaldehyde, processed and paraffin embedded. Sections were deparaffinized and stained with hematoxylin and eosin (H&E) for morphological analysis. Phenotype of smooth muscle and differentiated neurons was analyzed by incubating the sections in primary antibodies directed against smoothelin and β-III tubulin, respectively. Neuronal nitric oxide synthase (nNOS) and choline acetyltransferase (ChAT) antibodies were used to confirm the presence of inhibitory and excitatory motor neurons, respectively. Vascularization was confirmed by immunostaining of the sections with von Willebrand (vWF) factor. Appropriate fluorophore-conjugated secondary antibodies were used.

Circular strips of the harvested sphincters and gut tissues were also immediately obtained and evaluated for physiological functionality. A force transducer apparatus (Harvard Apparatus, Holliston, Mass.) was used to measure real time force generation. The tissues were hooked to a stationary fixed pin from one side and to the measuring arm of the force transducer from the other side. The tissues were kept in a warm tissue bath throughout the experiments. Establishment of basal tone by the sphincters, electromechanical coupling integrity of the smooth muscle of both the sphincters and the gut tissues, and the functionality of the differentiated neurons were evaluated.

Electromechanical coupling integrity was evaluated in the presence of 60 mM potassium chloride (KCl). Functionality of neurons was evaluated using electrical field stimulation (EFS) in the absence and presence of neurotoxin, tetrodotoxin (TTX) and nitric oxide synthase (nNOS) blocker $N_\omega$-Nitro-L-arginine methyl ester hydrochloride (L-NAME).

The difference in tensile strength, elongation at break and Young's modulus between the implants and the native rat intestines was evaluated by Student's t-test. Analysis of acquired force data was acquired using Powerlab and exported to GraphPad Prism 5.0 for Windows (GraphPad Software, San Diego, Calif.; www.graphpad.com). Second order Savitzky-Golay smoothing was applied to data. Student paired t-test was used to compare the means of forces in the absence and presence of inhibitors. All values were expressed as means±SEM. A p-value less than 0.05 was considered significant.

Figure 5B:
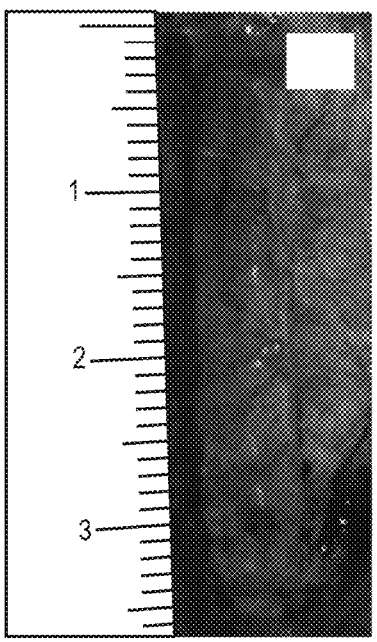
Figure 5C:
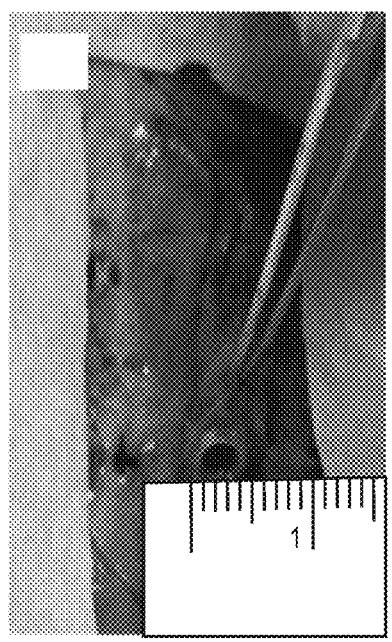

Results:

Gut-sphincter complex were engineered by combining innervated smooth muscle sheets and engineered innervated pyloric sphincters around tubular chitosan scaffolds (FIG. 5A). The engineered innervated smooth muscle sheets were wrapped circumferentially around the tubular scaffolds to form the circular muscle layer. The sheets constitute the gut part of the gut-sphincter complex. The engineered sphincters of the complex were placed at one end of the scaffolds. The bioengineered tissues were implanted subcutaneously in the abdomen of athymic rats for 4 weeks. At the end of 4 weeks implantation, the tissue engineered sphincter became integrated with the gut sphincter complex and formed a single continuous functional unit. The implants showed healthy pink color upon harvest (FIG. 5B). The implants were 3 cm in length and 0.5 cm diameter (FIG. 5C). The luminal patency of the implants was maintained for 4 weeks post-implantation. There were no signs of inflammation, infection or tissue necrosis. Neovascularization was visually demonstrated by the presence of blood vessels around the implants.

Figure 6A:
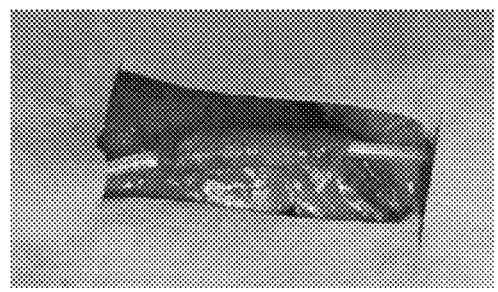
FIG. 6A is a photograph of a gut-sphincter complex measured for intraluminal pressures.
Figure 6B:
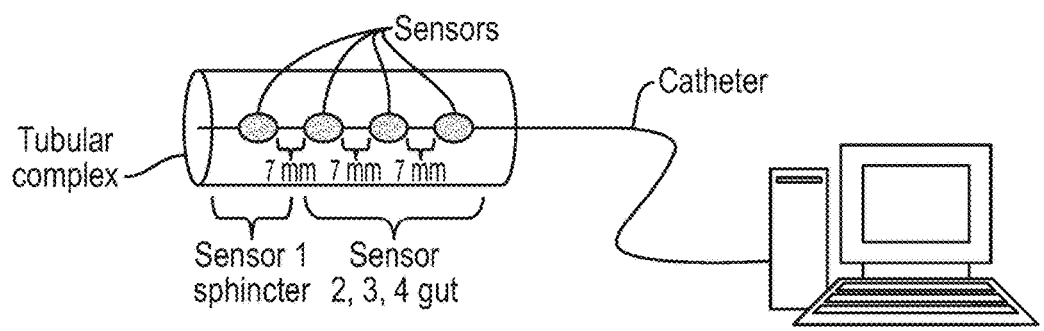
FIG. 6B is a schematic illustration of the intraluminal pressure measurement device and system used in FIG. 6A.
Figure 6C:
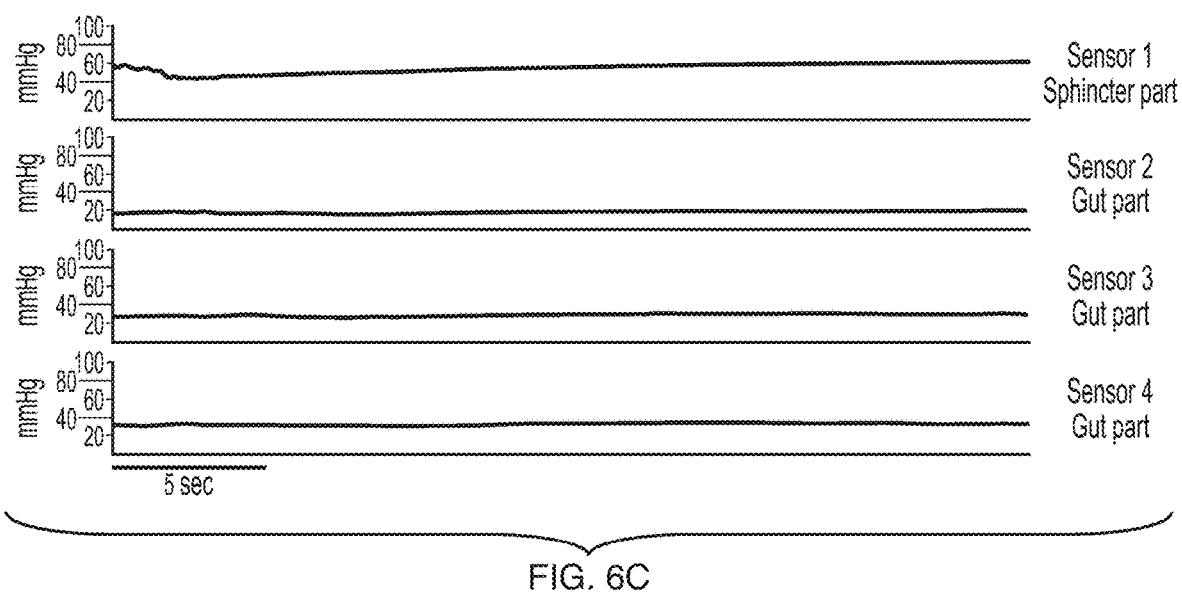
FIG. 6C is a graph of in vivo intraluminal pressure measurements. The rats were anesthetized and the complex was accessed. A catheter with 4 circumferential sensors was inserted into the complex to measure luminal pressure. The catheter was connected to Sandhill equipment that records the pressures (as shown in the diagram for each sensor). Mean gut luminal pressure was 21±2 mmHg while the sphincteric pressure was 52±3 mmHg.

The rats were anesthetized by continuous isoflurane masking. The implants were re-accessed. The catheter with circumferential sensors was calibrated before any measurement. The pressure reading was set to zero prior to insertion of the catheter into the lumen of the implant. The catheter was inserted into the lumen of the implant by increment of 1 sensor at a time until all sensors were inserted (FIGS. 6A-6C). Pressures started increasing as the catheter was inserted into the tissue. Pressure reading from each sensor was reflected on a separate channel. The catheter was inserted from the gut side of the implant (opposite end of the sphincter). Pressure reading of the sphincter is shown on the top graph (FIG. 6C). The other lower channels were measuring the gut part of the complex (FIG. 6C, lower three graphs). The mean luminal pressure (of all sensors) of the gut zone was (21±2 mmHg). The mean pressure recorded at the sphincter zone was (52±3 mmHg). The pressures were stable over time. The luminal patency was further confirmed by completely inserting the catheter through the length of the implant without obstruction.

Figure 7A:
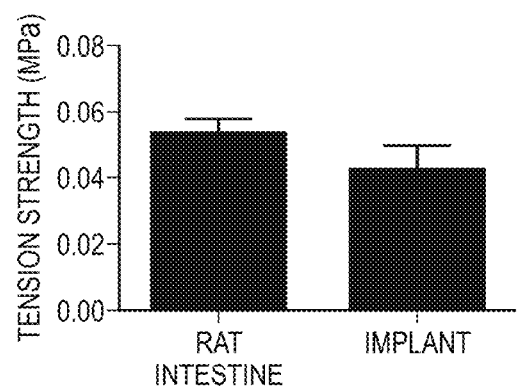
FIGS. 7A-7C are graphs showing the mechanical properties of the implanted complex. The tensile properties of the complex were lower than those of the native rat intestine; however they were not significantly different.
Figure 7B:
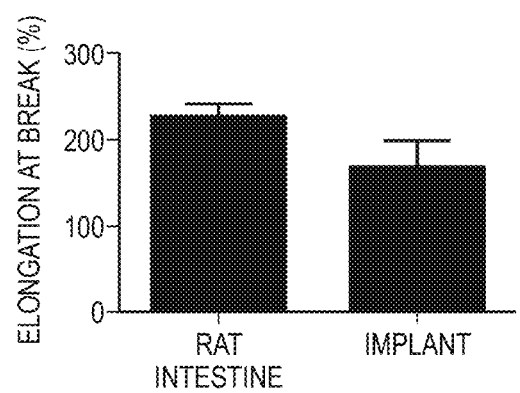
Figure 7C:
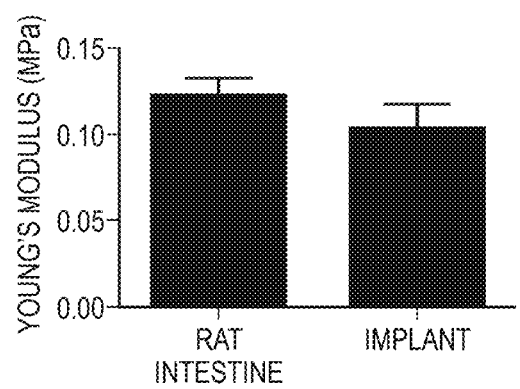

Uniaxial tensile properties of the implants were compared to those of native rat intestine. The tensile strength was significantly different between the implants and the native rat intestine (FIG. 7A). The tensile strength of the native rat intestine was 0.067±0.006 MPa whereas the average tensile strength of the implants was 0.043±0.007 MPa (n=4, p=0.02). Elongation at break (FIG. 7B) and Young's modulus (FIG. 7C) of the implants were lower than those of the native rat intestine, however, they were not significantly different (n=4, p=0.1 and p=0.37 respectively). Elongation at break and Young's modulus were 230±13% and 0.12±0.01 MPa, respectively for the native rat intestine. The implant's elongation at break and Young's modulus averaged 171±30% and 0.1±0.01 MPa, respectively.

A pressure transducer catheter with an inflatable balloon was inserted inside the lumen of the tubular implants. Pressure was increased gradually until failure of the implant. The pressure at failure was recorded as the burst pressure strength. The mean burst pressure strength of the implants was 1396±60 mmHg.

Figure 8A:
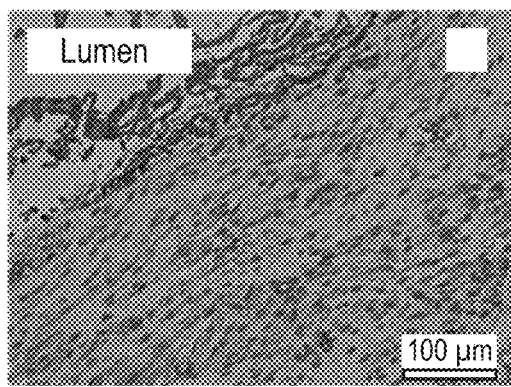
FIGS. 8A and 8B provide histological evaluations of the implants.
Figure 8B:
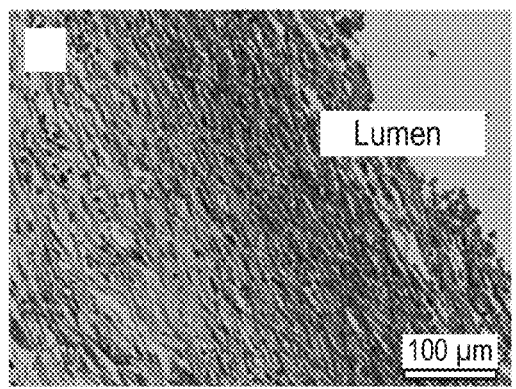

Paraffin cross sections of the harvested engineered sphincters and gut tissues of 6 μm thickness were prepared. Representative H&E staining of both the engineered sphincters and gut tissues after implantation is shown in FIGS. 8A and 8B, respectively. The engineered innervated smooth muscle sheets were wrapped circumferentially around the tubular scaffolds to form circular muscle layer. The smooth muscle of the engineered sphincters was also circumferentially aligned. H&E stains showed maintenance of smooth muscle alignment around the lumen of the tubular tissues for both the gut segment and the sphincter. H&E shows dense aligned smooth muscle.

Figure 9A:
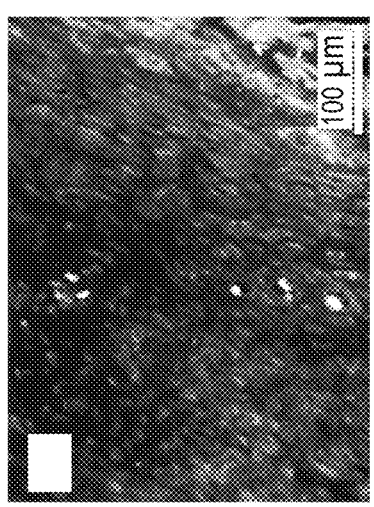
FIGS. 9A-9F are photographs showing the immunofluorescence of the implants.
Figure 9B:
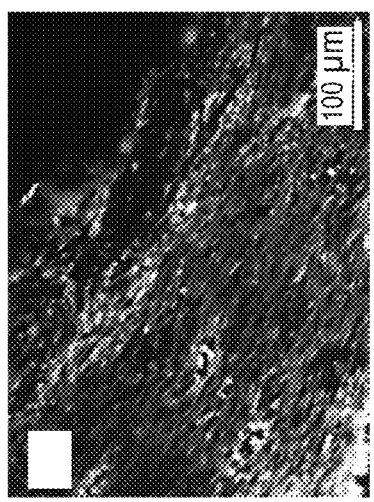
Figure 9C:
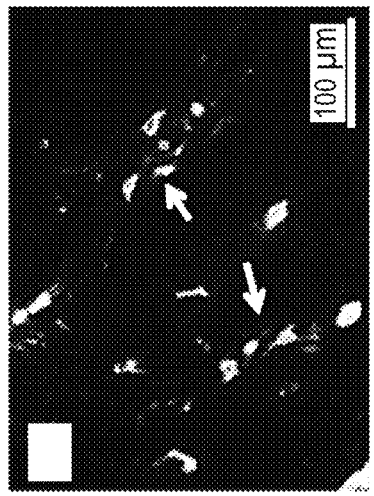
Figure 9D:
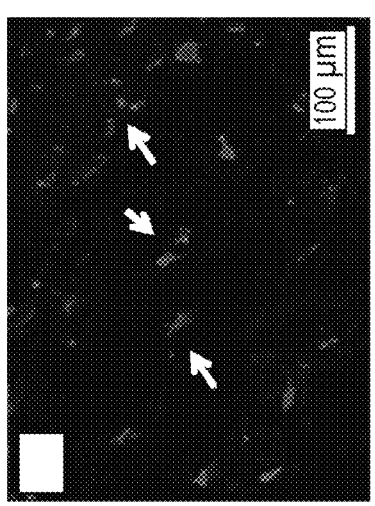
Figure 9E:
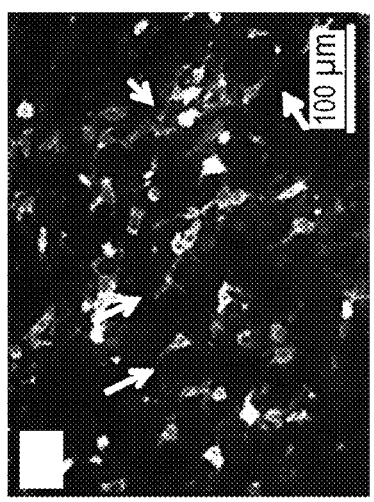
Figure 9F:
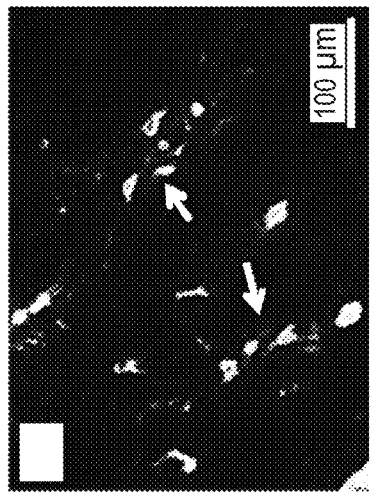

Sections of both the engineered sphincters and the engineered gut segments stained positive for the smooth muscle specific marker smoothelin (FIGS. 9A & 9B, respectively). This indicated that smooth muscle contractile phenotype of both the engineered sphincter and the gut segment was maintained over a period of 4 weeks post-implantation. Engineered tissues also stained positive for pan-neuronal marker, βIII-tubulin, indicating the presence of differentiated neurons in the engineered complex 4 weeks post-implantation (FIG. 9C). Additional positive staining for neural nitric oxide synthase (nNOS) (FIG. 9D) and choline acetyltransferase (ChAT) (FIG. 9E) indicate the presence of inhibitory and excitatory motor neurons in the implanted complex. Positive stain for Von Willebrand Factor (vWF) confirmed the vascularization of the implants (FIG. 9F).

Figure 10A:
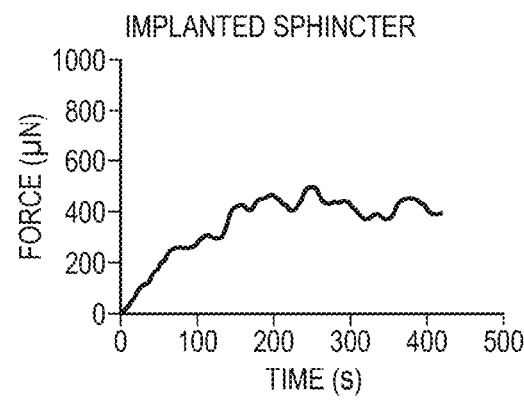
FIG. 10A-10C are graphs showing in vitro physiological functionality of the implants.
Figure 10B:
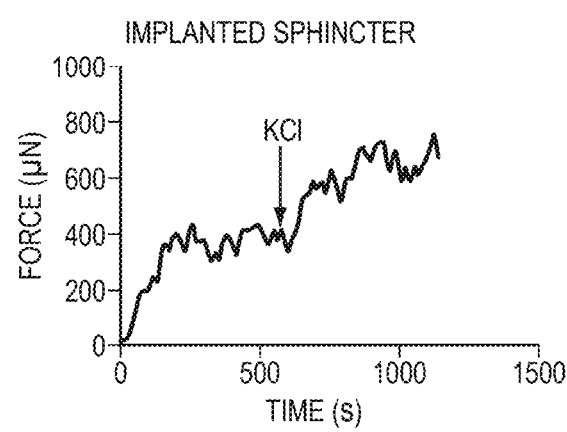
Figure 10C:
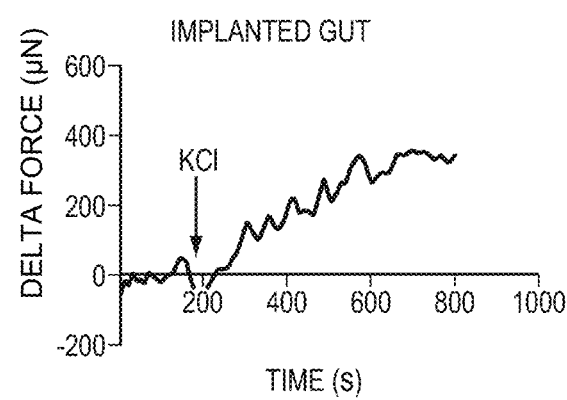

Circular strips of implanted engineered sphincter and gut segments were hooked to a force transducer measuring arm and allowed to establish baseline. The engineered sphincters exhibited the spontaneous ability to generate basal tone that averaged 382±79 μN (FIG. 10A). Electromechanical coupling integrity of both the sphincters and the gut segments was demonstrated by the robust contraction of the tissues after the addition of KCl. Sphincters demonstrated a contraction of 427±42 μN above the basal tone (FIG. 10B) while the gut tissues exhibited a mean peak contraction of 434±17 μN (FIG. 10C).

Figure 11A:
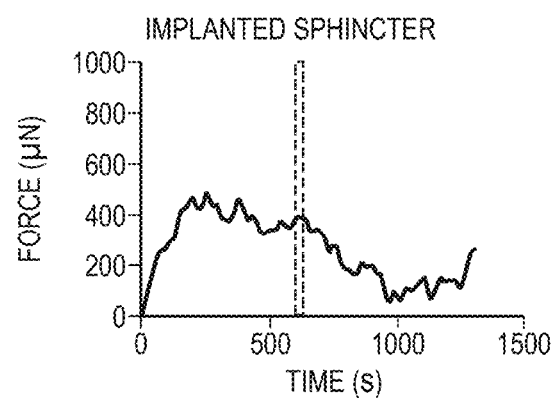
FIGS. 11A-11D are further graphs showing in vitro physiological functionality of the implants.
Figure 11B:
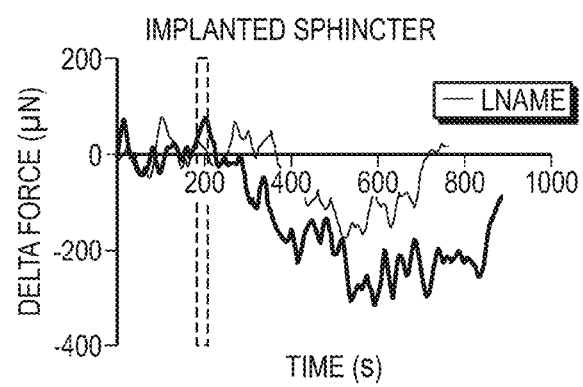
Figure 11C:
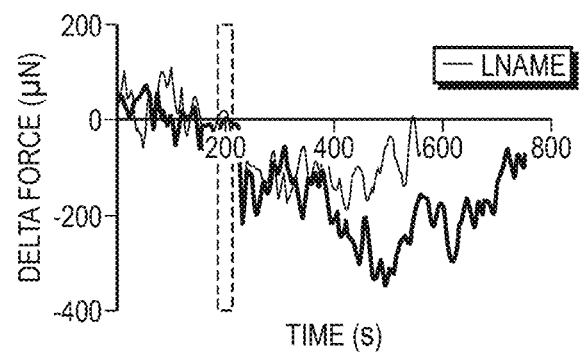
Figure 11D:
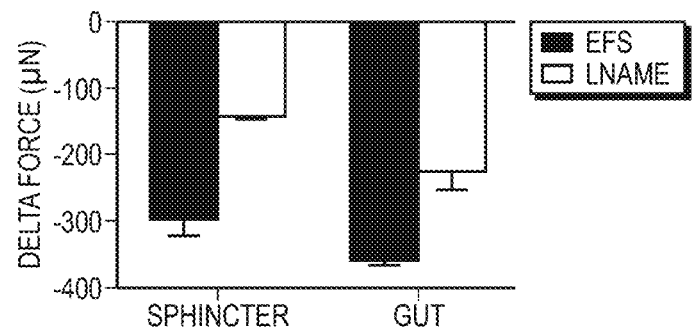

Functionality of neurons in the segment was evaluated by electrical field stimulation (8 Hz and 0.5 ms). Smooth muscle of both the implanted engineered sphincters and the gut segments relaxed following excitation of the nerves (FIG. 11). Relaxation of the implanted sphincters averaged −294±26 μN below the basal tone (FIGS. 11A and 11B—black traces) and the maximal relaxation averaged −355±8 μN in the gut segment (FIG. 11C—black trace). The tissues were then washed with fresh warm buffer and pre-treated with TTX. Upon excitation of the nerves, relaxation was completely abolished in both the sphincters and the gut segments. This indicated that the relaxation of the smooth muscle observed following EFS without TTX was due to excitation of neurons only. This also indicates that the neural progenitor cells within the complexes differentiated into functional neurons. Further characterization of the relaxation response was studied in the presence of nNOS inhibitor LNAME. The tissues were pre-treated with LNAME followed by EFS. Relaxation was significantly reduced to −140±6 µN in the sphincters (FIG. 11B—grey trace) and −223±29 in the gut segments (FIG. 11C—grey trace). This inhibition indicates that EFS-induced relaxation of the smooth muscle was partially mediated by functional nitrergic neurons. The data from FIGS. 11B and 11C are quantified in the bar graph depicted in FIG. 11D.

The teachings of all patents, published applications and references cited herein are incorporated by reference in their entirety.

While the preferred embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

The invention claimed is:

1. A method of forming a tissue engineered, tubular gut-sphincter complex comprising:
    isolating intestinal circular smooth muscle cells from an intestinal donor source,
    isolating sphincteric smooth muscle cells from a sphincteric donor source,
    isolating enteric neural progenitor cells from at least one neural progenitor donor source,
    seeding the isolated intestinal circular smooth muscle cells on a mold with a surface texture that induces longitudinal alignment of the intestinal circular smooth muscle cells,
    adding the isolated enteric neural progenitor cells to the intestinal circular smooth muscle cells on the mold,
    co-culturing the intestinal circular smooth muscle cells and the enteric neural progenitor cells until an innervated aligned smooth muscle sheet is obtained,
    disposing the innervated aligned smooth muscle sheet around a tubular scaffold to form an innervated intestinal tissue construct,
    admixing the sphincteric smooth muscle cells and additional enteric neural progenitor cells in a biocompatible gel solution,
    applying the gel and admixed cells to a mold having a central post;
    co-culturing the sphincteric smooth muscle cells and neural progenitor cells to form an innervated sphincter construct around the mold post,
    transferring and applying the innervated sphincter construct to the tubular scaffold such that the innervated intestinal tissue construct and the innervated sphincter construct contact each other, and
    further culturing the combined sphincter and intestinal tissue constructs about the scaffold until a unified tubular gut-sphincter complex is obtained.

2. The method of claim 1, wherein steps of isolating the intestinal circular smooth muscle cells, sphincteric smooth muscle cells and enteric neural progenitor cells further comprise obtaining each type of cell from a single subject.

3. The method of claim 1, wherein at least one co-culturing step comprises culturing cells in a collagen suspension.

4. The method of claim 1, wherein the step of disposing the innervated aligned smooth muscle sheet around a tubular scaffold comprises wrapping the innervated aligned smooth muscle sheet around a chitosan scaffold.

5. The method of claim 1, wherein the method further comprises connecting two or more innervated aligned smooth muscle sheets together to form a composite structure.

6. A tubular gut-sphincter complex formed by the method of claim 1.

* * * * *